United States Patent
Klettke et al.

(10) Patent No.: US 7,838,572 B2
(45) Date of Patent: Nov. 23, 2010

(54) DENTAL COMPOSITION COMPRISING ETHYLENE IMINE COMPOUNDS AND NON-REACTIVE ACCELERATORS

(75) Inventors: Thomas Klettke, Diessen (DE); Cornelia Fuehrer, Wertach (DE)

(73) Assignee: 3M Innovative Properties Company, St. Paul, MN (US)

(*) Notice: Subject to any disclaimer, the term of this patent is extended or adjusted under 35 U.S.C. 154(b) by 825 days.

(21) Appl. No.: 10/564,102

(22) PCT Filed: Jul. 16, 2004

(86) PCT No.: PCT/EP2004/007928
§ 371 (c)(1), (2), (4) Date: Jun. 19, 2006

(87) PCT Pub. No.: WO2005/013924
PCT Pub. Date: Feb. 17, 2005

(65) Prior Publication Data
US 2006/0247327 A1 Nov. 2, 2006

(30) Foreign Application Priority Data
Jul. 17, 2003 (EP) ................... 03016195

(51) Int. Cl.
*A61K 6/10* (2006.01)
(52) U.S. Cl. .................. 523/109; 528/424; 433/214
(58) Field of Classification Search ................ 523/109; 528/424; 433/214
See application file for complete search history.

(56) References Cited

U.S. PATENT DOCUMENTS

| | | | |
|---|---|---|---|
| 3,453,242 A | 7/1969 | Schmitt et al. | |
| 4,167,618 A | 9/1979 | Schmitt et al. | |
| 4,600,766 A | 7/1986 | Arita et al. | |
| 5,130,348 A | 7/1992 | Zahler et al. | |
| 5,286,105 A | 2/1994 | Herold et al. | |
| 5,569,691 A | 10/1996 | Guggenberger et al. | |
| 6,395,801 B1 | 5/2002 | Bissinger et al. | |
| 6,867,246 B2 | 3/2005 | Nowak et al. | |
| 6,894,144 B1 * | 5/2005 | Zech et al. ............... 528/394 |
| 2003/0109596 A1 | 6/2003 | Wanek et al. | |
| 2003/0153726 A1 | 8/2003 | Eckhardt et al. | |
| 2006/0106127 A1 | 5/2006 | Klettke et al. | |

FOREIGN PATENT DOCUMENTS

| | | |
|---|---|---|
| DE | 4306997 A1 | 9/1994 |
| DE | 19711514 A1 | 9/1998 |
| DE | 19753456 A1 | 6/1999 |
| DE | 10018918 A1 | 11/2001 |
| DE | 10026852 A1 | 12/2001 |
| DE | 10058846 A1 | 6/2002 |
| DE | 10235990.3 | 2/2004 |
| DE | 60300415 T2 | 3/2006 |
| EP | 0492413 B1 | 7/1992 |
| WO | WO 01/17483 * | 3/2001 |
| WO | WO 01/52792 A1 | 7/2001 |
| WO | WO 2005/013924 A1 | 2/2005 |

OTHER PUBLICATIONS

ASTM D2849 Method C, 1975.
DIN 50125, Apr. 1991, Jan. 2004.
DIN 53505, Jun. 1987, Aug. 2000.
DIN EN ISO 4823:2000, Mar. 1994, Aug. 2001.
G.D. Jones, D.C. MacWilliams, N.A. Braxtor, "Species in the Polymerization of Ethylenimine and N-Methylethylenimine", J. Org. Chem. vol. 30, 1965, pp, 1994-2003.
Houben-Weyl, "Methoden der organischen Chemie", 14/2, p. 17, Georg Thieme Verlag, Stuttgart, 1963.
O.C. Dermer, G.E. Ham "Ethylenimine and other Aziridines", Academic Press (1969).
Ullmanns Enzykopadie der technischen Chemie, 4. Auflage, Verlag Chemie, Weinheim, Band 24, p. 3, 1963.

* cited by examiner

*Primary Examiner*—Tae H Yoon
(74) *Attorney, Agent, or Firm*—Ann M. Mueting

(57) ABSTRACT

The present invention relates to a composition with enhanced speed of set, especially to a method of making rubber-like elastomers with improved hardening characteristics. In this respect the present invention provides a composition comprising with respect to the cured composition a ethylene imine group containing component A, a $SO_2$—NH group containing component B and an initiator C. Optionally additives like modifiers, fillers, dyes, pigments, thixotropic agents, flow improvers, polymeric thickeners, surfactants, odorous substances, diluters and flavorings can be added.

19 Claims, No Drawings

DENTAL COMPOSITION COMPRISING ETHYLENE IMINE COMPOUNDS AND NON-REACTIVE ACCELERATORS

The invention relates to a dental composition with enhanced speed of set, especially to a method of making rubber-like elastomers with improved hardening characteristics.

Compared to known ethylene imine group containing polyether materials, herein called slow-setting materials, the materials according to the invention have a shorter time of set. These formulations are called fast-setting materials.

Usually the speed of set of dental formulations is adjusted by varying the amount of reactive components, e.g. varying the amount of the polymerizable compound(s) and varying the amount the initiator(s) accordingly and/or varying the amount of the retarder(s).

Aziridines which are also known as ethylene imine compounds can be converted into highly molecular polyamine compounds by means of catalysts which introduce and thus initiate polymerization.

In this respect U.S. Pat. No. 3,453,242 describes curable elastomers from polyethers and ethylene imine derivatives. The polymers are substantially linear in structure and contain ethylene imine groups especially at the ends of the chain to obtain rubber-like products.

DE 100 58 846 A1, DE 197 53 456 A1, DE 100 18 918 A1 describe formulations containing polyether aziridines which show regular setting behavior.

For instance DE 100 58 846 A1 describes the use of N-alkyl aziridino polyethers containing methyl groups in the side chain to improve the properties of the uncured pastes at low temperatures. It is also described that 1 to 35% by weight of solvents may be used related to the cured material. The solvents are chosen from the group of polyester polyols, aliphatic esters, oils, fats, aliphatic hydrocarbons, one- or multifunctional esters of multibasic acids, esters or amides of sulphonic acids.

DE 197 53 456 A1 mentions that solvents from 0 to 95% by weight (related to the cured material) selected from polyetherpolyols, polyesterpolyols, polycarbonate polyols, aromatic hydrocarbons, araliphatic hydrocarbons, one- or multifunctional esters of multibasic acids, esters or amides of sulphonic acids may be used.

DE 100 18 918 A1 describes formulations of catalyst pastes. The catalyst pastes contain 0 to 95% by weight of an inert solvent chosen from the group of polyether polyols, polyester polyols, aliphatic esters, oils, fats, waxes, aliphatic hydrocarbons, araliphatic hydrocarbons, one- or multifunctional esters of multibasic acids, esters or amides of sulphonic acids. The formulations comprise water (0.1 to 20%) which is used to influence the speed of set and other properties of the catalyst paste and the cured rubber.

It is also described that the addition of water to a system of N-alkyl ethylene imines, solvent and initiators alters the speed of set and the conversion rate (G. D. Jones, D. C. MacWilliams, N. A. Braxtor J. Org. Chem. 1965, 1994-2003). The addition of water to uncured polyether precision impression materials, however, may cause sticky surfaces when the impression is cured in the presence of additional water (or saliva in mouth) and may also negatively influence the precision of the impression when impregnated retraction cords or retraction solutions are used.

A further possibility to enhance the speed of set of formulations comprising compounds having aziridino groups is the additional use of monofunctional compounds together with multifunctional compounds.

In this respect the German patent application DE 10235990.3 describes a composition, wherein at least one compound has at least two ethylene imine groups and at least one compound has one ethylene imine group. However, the additional use of compounds having one ethylene imine group requires the increase of initiator. The increase of ethylene imine concentration and initiator results in high costs.

Impression materials based on polyvinyl siloxanes with short setting times are also known. Examples are Splash™ Half-Time (Discus), Aquasil™ Fast Set (Dentsply/Caulk), Imprint™ II Quick Step (3M ESPE AG), Take 1 Fast Set (Kerr), Extrude Extra (Kerr).

However, up to now there is no fast-setting polyether, especially no ethylene imine containing material available.

Considering the clinical situation, in most cases precision impression materials are used to obtain impressions of crowns, inlays, small implants or small bridges (approx. 80%). In all these cases the dentist does not need a long total working time. In addition a short oral setting time also would be advantageous. Shortening both working time and oral setting time would save time for the dental professionals. Shortening of the whole rather uncomfortable impression taking would be advantageous to the patient.

It is thus an object of the invention to alleviate one or more of the problems mentioned above.

It is also an object of the invention to provide a composition with improved properties.

It is another object of the invention to provide a composition, especially a dental polyether composition with enhanced speed of set without essentially altering the elastomeric properties of the cured material.

It has been found that one or more of the above mentioned objects can be achieved by providing a composition as described in the text below.

In this respect the invention relates to a curable dental composition comprising
- an ethylene imine group containing component A, especially an N-alkyl aziridine polyether,
- a $SO_2$—NH group containing component B, comprising e.g. N-alkyl or N-aryl substituted aryl sulfonic acid amides and/or N-alkyl or N-aryl substituted alkyl sulfonic acid amides and non N-substituted sulfonic acid amides,
- an initiator C able to start the curing process of component A,
- optionally additives D like modifiers, fillers, dyes, pigments, thixotropic agents, flow improvers, polymeric thickeners, surfactants, odorous substances, diluting agent(s) and flavourings.

Surprisingly it has been found that by adding a non-reactive accelerator the speed of set of the composition to be hardened can be accelerated without affecting the elastomeric properties of the vulcanized formulation to a considerable extent.

Adding such a $SO_2$—NH group containing component to a curable ethylene imine group containing component enables one to provide compositions that are accelerated with respect to the speed of set without essentially varying the amount of reactive components. The $SO_2$—NH group containing component usually does not alter the physical properties of the cured material to a considerable extent.

Using N,N-disubstituted sulfonic acid amides as component B, that is components containing only a $SO_2$—NR2 group, wherein R is not H and thus not comprising a $SO_2$—NH group with an N—H valence, is not preferred.

Without wishing to be limited to any particular mechanism, it is believed that without at least one NH moiety in the sulfonic acid amid group, not all of the effects intended to be achieved can be reached.

Using the present invention, formulations can be provided fulfilling the requirements according to DIN EN ISO 4823:

2000 of Type 0 (kneadable), Type 1 (high viscosity), Type 2 (medium viscosity), and Type 3 (low viscosity).

The invention provides means to realize short(er) working times of curable compositions, especially dental impression materials, at room temperature and short oral setting times. A total working time at room temperature (23° C.) of less than 3:00 min according to DIN EN ISO 4823:2000 and an oral setting time of less than 3:30 min can be realized.

The total working time at room temperature (23° C.) can be measured according to DIN EN ISO 4823:2000. For instance, for Impregum™ Garant L DuoSoft and Permadyne Garant L 2:1 (3M ESPE AG), both Type 3 regular setting polyether precision impression materials, a working time of 3 min 40 s±15 s and 4 min±15 s, respectively, is measured.

The oral setting time is given by the manufacturer in the instructions for use. According to DIN EN ISO 4823:2000 the elastomeric property recovery from deformation of the vulcanized material have to reach values of ≧96.5% within the recommended oral setting time. In addition according to DIN EN ISO 4823:2000 the elastomeric property strain in compression of the vulcanized material has to come up to a value within the range of 0.8 to 20.0% for Type 0 and Type 1 materials and in the range of 2.0 to 20.0% for Type 2 and Type 3 materials, respectively within the recommended oral setting time.

For instance, for Permadyne™ Garant L 2:1 and Impregum™ Garant L DuoSoft (3M ESPE AG), both Type 3 regular setting polyether precision impression materials an oral setting time of 3 min 30 s is advised by the manufacturer.

Often dental formulations are provided as two-compartment systems in which the two pastes are stored separately. The base paste contains the polymerizable compound(s) and is stored separately from the catalyst paste which contains the initiator.

With respect to shelf-life it is an advantage that the non-reactive accelerators used according to the invention are compatible with the polymerizable compound(s) and with the initiator(s), as well.

An additional paste containing at least one accelerator might also be provided which can be used in dental offices to enhance the setting time of a given polyether impression material according to the dentists needs.

The invention provides therefore a low-cost and low-risk method to provide a quick-setting polyether impression material.

The terms "comprise" and "contain" within the meaning of the invention introduce a non exhaustive list of features. Likewise, the word "one" or "a" is to be understood in the sense of "at least one".

"Working time" according to the invention is the period between complete mixing of the components and the incipient curing of the mixed composition at room temperature. The end of the working time is regarded as the time at which a mixed composition displays pronounced changes such as skin formation or greatly reduced flowability. At the end of the working time the consistency of the mixed material does not allow the making of a precision impression with the desired detail reproduction and dimensional properties.

"Oral setting time" according to the invention can be defined as the period between placing the dental tray in the mouth of the patient (the impression material is still processable) and the removal of the dental tray at the time the vulcanized impression material shows the desired elastomeric properties.

As N-alkyl aziridine polyether (ethylene imine group containing) component A every component can be used which can be vulcanized in the presence of initiator C. The ethylene imine group containing component A comprises at least one ethylene imine group, preferably at least two ethylene imine groups. Those components are know and described e.g. in U.S. Pat. No. 3,453,242, DE 100 58 846 A1, DE 197 53 456 A1, DE 100 18 918 A1 and are generally known as N-alkyl aziridine polyether compositions.

Suitable components A are N-alkyl substituted aziridines attached to oligomeric and/or polymeric hydrocarbon, ester, ether or siloxane. The attached N-alkyl aziridene can be represented by the formula

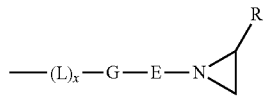

wherein

R represents H, $C_1$-$C_{12}$ alkyl, $C_2$-$C_{12}$ alkenyl, $C_2$-$C_{12}$ alkinyl, $C_7$-$C_{15}$ alkylaryl, $C_7$-$C_{15}$ arylalkyl, $C_3$-$C_{12}$ cycloalkyl, and wherein hydrogen atoms may be replaced by Cl or F and/or wherein up to five carbon atoms may be replaced by atoms or group of atoms selected from O, CO, N, S, E represents a $C_1$-$C_{18}$ branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)(CH$_2$)$_m$C(O) with m=1 to 10, C(S)NR, CH$_2$, L represents O, S, NR with x=0 or 1.

Component A can be present in an amount in the range of about 10 to about 90% by weight with respect to the cured composition.

For an impression material component A can be present in an amount in the range of about 35 to about 90% by weight, or in an amount in the range of about 40 to about 75% by weight with respect to the cured composition.

For a of a duplicating material component A can be present in an amount in the range of about 10 to about 25% by weight, or in an amount in the range of about 12 to about 20% by weight with respect to the cured composition.

The molecular weight ($M_N$) of component A before setting can be in the range of about 600 to about 20.000 g/mol, or in the range of about 1.000 to about 10.0000 g/mol, determined with GPC. Appropriate methods are know by the expert. In addition the determination of the molecular weight is possible using nuclear magnetic resonance spectroscopy (end-group determination). There are also applicable methods described in the literature for organic polyols that may be used like determination of hydroxyl number according to Houben-Weyl, "Methoden der organischen Chemie", 14/2, page 17, Georg Thieme Verlag, Stuttgart, 1963 or according to AS™ D2849 Method C.

A very useful method for determination of the molecular weight organic polyols is a GPC method using a combination of PSS SDV 10.000 Å+PSS SDV 500 Å with column dimensions 8×300 mm and a particle size of 5 μm. In addition a pre-column PSS SDV 100 Å with column dimensions 8×50 mm and a particle size of 10 μm is used. The eluent is THF stabilized with Jonol running with a flow rate of 1.0 ml/min. The detector is a refractive index detector (RI), the injection volume 100 μl. The samples have a concentration of 1% (solvent THF). Polystyrol standards are used as the reference.

As SO$_2$—NH group containing component B every component can be used, which is able to accelerate the speed of set of component A.

A sufficient acceleration of setting (measured at room temperature) of an impression material can be achieved, if e.g. 4.0% by weight of a non-reactive diluter of a given formulation is replaced by the same amount of component B with the result that the Shore Hardness A (mean value determined from at least three samples) measured after 6 min according to DIN EN ISO 53505 increases by more than about 30%, or by more than about 40%, or by more than about 50% with respect to the value measured for the formulation without component B. Alternatively, e.g. 4.0% by weight of component B may be added to a given formulation to attain the desired acceleration of set. For very soft rubbers like duplicating materials the acceleration in setting may be measured using a common oscillating rheometer monitoring G' and G".

$SO_2$—NH group containing component B comprises at least one $SO_2$—NH group, if needed at least two $SO_2$—NH groups. The $SO_2$—NH group containing component B can be a molecular or polymeric compound.

Suitable components B are N-substituted aryl sulfonic acid amides or N-substituted alkyl sulfonic acid amides and non N-substituted alkyl or aryl sulfonic acid amides, that is sulfonic acid amides comprising a $SO_2$—$NH_2$ group. In the sulfonamides one hydrogen atom attached to the nitrogen atom of the sulfonamide group can be replaced by an alkyl or aryl radical.

Component B can be represented e.g. by one of the following formulas:

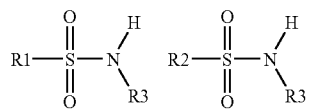

wherein

R1 represents $C_1$-$C_{22}$ alkyl, $C_2$-$C_{22}$ alkenyl, $C_2$-$C_{22}$ alkinyl, $C_7$-$C_{22}$ arylalkyl or $C_3$-$C_{22}$ cycloalkyl, and wherein one or more hydrogen atoms may be replaced by Cl or F and/or up to five carbon atoms may be replaced by atoms or group of atoms selected from O, CO, N, S, R2 represents $C_6$-$C_{18}$ aryl, $C_7$-$C_{22}$ alkylaryl, $C_2$-$C_{22}$ cycloalkylaryl, $C_7$-$C_{22}$ alkenylaryl or $C_7$-$C_{22}$ alkinylaryl, wherein one or more hydrogen atoms may be replaced by Cl or F and/or up to five carbon atoms may be replaced by atoms or group of atoms selected from O, CO, N, S, R3 represents R1 or R2.

Also polymeric substances comprising the following structure may be used:

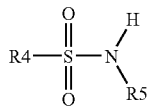

wherein R4 is R1 or R2, and wherein R5 represents the chemical linkage to the polymer.

Component B contains preferably a sulfonic acid amide or mixture of sulfonic acid amides comprising an aromatic moiety, more preferably a structural element as described in the formula below

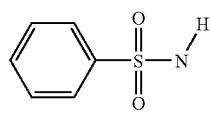

wherein the aromatic ring may be substituted by one or more substituents.

The sulfonic acid amide can be used alone or in admixture with other different sulfonic acid amides.

Particularly preferred are benzene sulfonic acid N-butyl amide, p-toluene sulfonic acid N-ethyl amide or a mixture of o-/p-toluene sulfonic acid N-ethyl amide.

Component B can be present in an amount in the range of about 0.01 to about 20.0, or in the range of about 0.1 to about 10.0, or in the range of about 0.2 to about 6.0% by weight with respect to the cured composition.

The molecular weight of component B can be in the range of about 90 to about 2000 $gmol^{-1}$ or in the range of about 90 to about 300 $gmol^{-1}$.

As initiator C every component can be used, which is able to start the curing process of component A.

The molar ratio between the initiator and the N-alkyl substituted aziridines of the formulation usually is in the range of $gmol^{-1}$ from about 1.0:0.1 to about 1.0:20.0, or in the range of about 1.0:0.5 to about 1.0:10.0, or in the range from about 1.0:0.8 to about 1.0:3.0.

Suitable initiators can be found in O. C. Dermer, G. E. Ham "Ethylenimine and other Aziridines" Academic Press (1969).

Particularly useful are the substituted alkyl sulfonium salts described in U.S. Pat. No. 4,167,618 incorporated herein by reference.

Optionally additives like modifiers, fillers, dyes, pigments, thixotropic agents, flow improvers, polymeric thickeners, surfactants, odorous substances, diluters and flavourings can be added. Additional substances might be useful to further adjust the rheological characteristics.

The additive(s) can be present in an amount in the range of about 10 to about 90% by weight with respect to the cured composition. For impression materials the additive(s) can be present in an amount in the range of about 10 to about 65%, or in the range of about 25 to about 60% with respect to the cured composition. For duplicating materials the additive(s) can be present in the range of about 10 to about 90%, or in the range of about 20 to about 85% by weight with respect to the cured composition.

Suitable filler(s) are e.g. alumosilicates, silicic acids, quartz powder, wollastonite, mica powder and diatomaceous earth.

Suitable thixotropic agent(s) are e.g. surface treated silica and/or waxes according to the definition in Ullmanns Enzyklopädie der technischen Chemie, 4. Auflage, Verlag Chemie, Weinheim, Band 24, page 3. Especially useful are triglycerides as described in DE 197 11 514 A1.

Suitable surfactant(s) are polyethers and polyether type materials with special structures such as Pluronic™, Synperonic™, Silwet™ type materials. Especially useful are substances described in DE 43 06 997 A1.

Suitable diluting agent(s) are liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, aromatic and aliphatic esters of sulfonic acids like Mesamoll™, derivatives of di- and tri-ethylen and -propylene glycol, typical aromatic diluters like poly phenyls, dibenzyl toluene, xylyl toluene, dixylyl toluene and polymeric compounds like polyethers, polyesters, polycarbonates, polyolefines. From the group of polymeric compounds, compounds with hydroxyl, ether, alkyl, ester functions are preferred.

The shore hardness A of the compositions of the invention is measured according to DIN 53505. To monitor the speed of set time-dependent measurements were performed.

The shore hardness A measured after 24 hours usually is in the range from about 40 to about 80 for impression materials and in the range from about 10 to about 40 for duplicating materials.

The elongation at break according to DIN 50125 of the cured impression material of the invention measured 24 hours after mixing the components usually is ≧ about 40%, or ≧ about 50% or ≧ about 60%.

The tensile strength according to DIN 50125 of the cured impression material of the invention measured 24 hours after mixing the components usually is ≧ about 0.50 MPa, or ≧ about 0.55 MPa or ≧ about 0.60 MPa.

The elongation at break according to DIN 50125 of the cured duplicating material of the invention measured 24 hours after mixing the components usually is ≧ about 80%, or ≧ about 100% or ≧ about 120%.

The tensile strength according to DIN 50125 of the cured dublicating material of the invention measured 24 hours after mixing the components usually is ≧ about 0.20 MPa, or ≧ about 0.25 MPa or ≧ about 0.30 MPa.

As mentioned above dental formulations are often provided as two-component systems.

Therefore, the invention also relates to a kit of parts, wherein the base part comprises component A, the catalyst part comprises component C, and wherein component B is present either in the base part or the catalyst part or in the base part and the catalyst part.

However, the accelerating effect of component B can also be used to enhance the speed of set of component A containing compositions described in the state of the art.

Presently, the following components are available on the market: Materials of Type 1, (comparable to Permadyne™ Penta™ H, Permadyne™ fest, Impregum™ Penta™ H DuoSoft™), Type 2 (comparable to Impregum™ F, Impregum™ Penta™, Impregum™ Penta™ Soft) and Type 3 (comparable to Permadyne™ Penta™ L, Permadyne™ Garant™ 2:1, Permadyne™ dünn, Impregum™ Penta™ L DuoSoft™, Impregum™ Garant™ L DuoSoft™). All materials are available from 3M ESPE AG.

Therefore, the invention relates also to a kit of parts, wherein component B is comprised in a further part and neither comprised in the catalyst part nor in the base part.

The invention also relates to a method of producing a curable composition comprising the steps a) providing components A, B and C, b) mixing the components.

The dosing of the components can be carried out by sight (strand-length comparison), by weight, via pre-dosed pack units and subsequent manual mixing, from double-chambered cartridges with static mixing tubes or by means of volume dosing systems with downstream static or dynamic mixers.

A mixing device can be used as it is described in EP 0 492 413 B1 and available on the market as Pentamix™ or Pentamix™ 2. Mixing, however, can also be achieved manually.

A further subject of the invention are packages containing components of the composition, in particular cartridges, bags, prefilled dental trays.

The composition according to the invention can advantageously be used for modeling of objects or body parts. The composition of the invention is particularly useful as in the dental field, e.g. as impression material, especially as a precision impression material, as a bite registration material or duplicating material.

The composition of the invention does not necessarily comprise water.

In addition the composition does not necessarily comprise sulfonamides used as active agents in drugs or herbicides.

The invention is hereinafter described by examples. The examples are not intended to limit the scope of the invention.

Measurements

Measuring Shore Hardness A is a very convenient method to obtain data about the degree of vulcanization. The value of Shore Hardness is a common number in dentistry to characterize the vulcanized impression. Time dependant measurements were done according to DIN 53505. For determination of the values three independent measurements were performed. A "Handhärteprüfgerät Zwick 3150" (Zwick GmbH &Co, Ulm) was used as the measuring device. The accuracy of the given values is ±1.

Tensile strength and elongation at break were measured according to DIN 50125 Form B. The sample was 6.0±0.1 mm in diameter and 50.0±0.1 mm in lengths (Zugprobe B 6×50 DIN 50125). For determination of the values five independent measurements were performed. A "Universalprüfmaschine Zwick 1435" (Zwick GmbH &Co, Ulm) was used as the measuring device.

Formulations:

| Base Paste 1 | |
|---|---|
| 81.0% | difunctional aziridino polyether (EO (ethylene oxide)/ THF (tetra hydro furan) polyether back bone; Mn: 6000) |
| 7.0% | fat (triscacylic ester of glycerine) |
| 1.0% | surfactant (copolymer EO/PO) |
| 9.5% | dibenzyl toluene |
| 1.5% | diatomaceous earth |

| Base Paste 2 | |
|---|---|
| 81.0% | difunctional aziridino polyether (Mn: 6000) |
| 7.0% | fat (triscacylic ester of glycerine) |
| 1.0% | surfactant (copolymer of EO/PO) |
| 8.8% | dibenzyl toluene |
| 1.5% | diatomaceous earth |
| 0.7% | imidazole compound |

| Catalyst Paste 1 | |
|---|---|
| 14.0% | sulfonium salt tetafluoroborate |
| 20.0% | acetyl tributyl citrate |
| 29.0% | unreactive polyether (Mn: 6000) |
| 12.0% | dibenzyl toluene |
| 3.0% | surfactant (copolymer EO/PO) |
| 11.0% | diatomaceous earth |
| 11.0% | highly dispersed silica, surface treated |

| Catalyst Paste 2 | |
|---|---|
| 13.5% | sulfonium salt tetafluoroborate |
| 19.0% | acetyl tributyl citrate |
| 29.0% | unreactive polyether (Mn: 6000) |
| 6.5% | dibenzyl toluene |
| 3.0% | surfactant (copolymer EO/PO) |
| 24.0% | diatomaceous earth |
| 5.0% | highly dispersed silica, surface treated |

I. Varying the Amount of Sulfonamide

A) 2.0 g of Base Paste 1 was mixed together with 1.2 g of Catalyst Paste 2, Entry 1. Di-benzyl toluene (CAS-No 26898-17-9) in the base paste was replaced by the same amount of bezene sulfonic acid N-butyl amide (CAS-No 3622-84-2), Entry 2-5.

TABLE 1

| Entry | Amount of benzene sulfonic acid N-butyl amide in Elastomer | Amount of benzene sulfonic acid N-butyl amide in Base Paste | Shore-Hardness A after 6 min | 8 min | 10 min | 15 min | 30 min | 24 h |
|---|---|---|---|---|---|---|---|---|
| 1 | 0.00% | 0.00% | 27 | 37 | 42 | 49 | 52 | 53 |
| 2 | 1.25% | 2.00% | 38 | 45 | 48 | 51 | 53 | 53 |
| 3 | 2.50% | 4.00% | 41 | 47 | 50 | 53 | 54 | 54 |
| 4 | 3.75% | 6.00% | 46 | 49 | 51 | 53 | 54 | 54 |
| 5 | 5.00% | 8.00% | 47 | 50 | 51 | 53 | 54 | 54 |

TABLE 2

| Entry | Amount of benzene sulfonic acid N-butyl amide Elastomer | Amount of benzene sulfonic acid N-butyl amide Base Paste | Tensile Strength | Elongation at break |
|---|---|---|---|---|
| 1 | 0.00% | 0.00% | 1.04 ± 0.03 MPa | 78 ± 6% |
| 3 | 2.50% | 4.00% | 0.99 ± 0.05 MPa | 75 ± 8% |
| 5 | 5.00% | 8.00% | 1.12 ± 0.15 MPa | 91 ± 23% |

B) The 2.0 g of altered Base Paste 1 that already contains 8.00% of benzene sulfonic acid N-butyl amide (CAS-No 3622-84-2) was used together with 1.2 g of Catalyst Paste 2, Entry 5.

Acetyl tributyl citrate (CAS-No 77-90-7) in the Catalyst Paste 2 was replaced by the same amount of benzene sulfonic acid N-butyl amide (CAS-No 3622-84-2). 2.0 g of the base paste according to Entry 5 was used with 1.2 g of the altered catalyst pastes, Entry 6-7.

TABLE 3

| Entry | Amount of benzene sulfonic acid N-butyl amide in Elastomer | Base Paste | Catalyst Paste | Shore-Hardness A after 6 min | 8 min | 10 min | 15 min | 30 min | 24 h |
|---|---|---|---|---|---|---|---|---|---|
| 5 | 5.00% | 8.00% | 0.00% | 47 | 50 | 51 | 53 | 54 | 54 |
| 6 | 6.25% | 8.00% | 3.33% | 47 | 50 | 52 | 53 | 53 | 53 |
| 7 | 7.50% | 8.00% | 6.67% | 48 | 51 | 53 | 53 | 53 | 53 |

The addition of component B does not necessarily have a significant effect on the elastomeric properties of the cured composition. Tensile strength and elongation at break remain essentially unchanged.

As can be inferred especially from Table 1 a sufficient Shore Hardness A can be achieved after a shorter period of time, if component B is present in the composition.

The desired effect can be already achieved at a considerable low concentration of the sulfonamide component. Further increasing the concentration does not necessarily enhance the speed of set.

II. Comparison: Sulfonamide Used in the Catalyst Paste Vs. Sulfonamide Used in the Base Paste Base Paste 2 and Catalyst Paste 1 were altered. 2.0 g of the used base paste was mixed together with 1.1 g catalyst.

Di-benzyl toluene (CAS-No 26898-17-9) in the base paste was replaced by the same amount of bezene sulfonic acid N-butyl amide (CAS-No 3622-84-2), Entry 8.

Acetyl tributyl citrate (CAS-No 77-90-7) in the catalyst paste was replaced by the same amount of bezene sulfonic acid N-butyl amide (CAS-No 3622-84-2), Entry 9.

TABLE 4

| | | Amount of benzene sulfonic acid N-butyl amide in | | Shore-Hardness A after | | | | | |
|---|---|---|---|---|---|---|---|---|---|
| Entry | Elastomer | Base Paste | Catalyst Paste | 6 min | 8 min | 10 min | 15 min | 30 min | 24 h |
| 8 | 2.26% | 3.50% | 0.00% | 28 | 36 | 40 | 45 | 46 | 47 |
| 9 | 2.26% | 0.00% | 6.40% | 29 | 36 | 40 | 43 | 48 | 49 |

Usually there is no significant difference whether the sulfonamide is used in the base paste or in the catalyst paste.

III. Comparison: Use of Mixture of o-/p-Toluene Sulfonic Acid N-Ethyl Amide Vs. Use of Bezene Sulfonic Acid N-Butyl Amide and D-Toluene Sulfonic Acid N-Ethyl Amide 2.0 g Base Paste 2. was mixed together with 1.2 g of Catalyst Paste 2, Entry 10.

Base Baste 2 was altered. 2.0 g of altered Base Paste 2 was mixed together with 1.2 of Catalyst Paste 2.

Di-benzyl toluene (CAS-No 26898-17-9) in the base paste was replaced by the same amount of mixture approx. 70:30 mixture of o-/p-toluene sulfonic acid N-ethyl amide (CAS-No 8047-99-2, 26914-52-3), Entry 11.

Di-benzyl toluene (CAS-No 26898-17-9) in the base paste was replaced by the same amount of bezene sulfonic acid N-butyl amide (CAS-No 80-39-7), Entry 12.

Di-benzyl toluene (CAS-No 26898-17-9) in the base paste was replaced by the same amount of bezene sulfonic acid N-butyl amide (CAS-No 3622-84-2), Entry 13.

TABLE 5

| | | Amount of Sulfonamide in | | Shore-Hardness A after | | | | | |
|---|---|---|---|---|---|---|---|---|---|
| Entry | Used sulphonamide | Elastomer | Base Paste | 6 min | 8 min | 10 min | 15 min | 30 min | 24 h |
| 10 | None | 0.00% | 0.00% | 16 | 28 | 34 | 42 | 48 | 50 |
| 11 | o-/p-toluene sulfonic acid N-ethyl amide | 3.75% | 6.00% | 31 | 38 | 41 | 46 | 49 | 50 |
| 12 | p-toluene sulfonic acid N-ethyl amide | 3.75% | 6.00% | 34 | 40 | 42 | 47 | 50 | 51 |
| 13 | benzene sulfonic acid N-butyl amide | 3.75% | 6.00% | 30 | 37 | 42 | 46 | 50 | 50 |

IV. Comparison: Use of Bezene Sulfonic Acid N-Butyl Amide Vs. Benzene Sulfonic Acide Amide Base Paste 2 was altered. 2.0 g of altered Base Paste 2 was mixed together with 1.2 g of Catalyst Paste 2.

Di-benzyl toluene (CAS-No 26898-17-9) in the base paste was replaced by the same amount of bezene sulfonic acid N-butyl amide (CAS-No 3622-84-2), Entry 13.

Di-benzyl toluene (CAS-No 26898-17-9) in the base paste was replaced by the same amount of benzene sulfonic acid amide (CAS-No 98-10-2), Entry 14.

TABLE 6

| Entry | Used sulphonamide | Amount of Sulfonamide in Elastomer | Amount of Sulfonamide in Base Paste | Shore-Hardness A after 6 min | 8 min | 10 min | 15 min | 30 min | 24 h |
|---|---|---|---|---|---|---|---|---|---|
| 13 | benzene sulfonic acid N-butyl amide | 3.75% | 6.00% | 30 | 37 | 42 | 46 | 50 | 50 |
| 14 | benzene sulfonic acid amide | 3.75% | 6.00% | 33 | 40 | 42 | 47 | 49 | 49 |

V. Comparison: Use of Benzene Sulfonic Acid N-Butyl Amide Vs. Benzene Sulfonic Acid N-Butyl N-Methyl Amide Base Paste 2 was altered. 2.0 g of altered Base Paste 2 was mixed together with 1.2 g of Catalyst Paste 2.

Di-benzyl toluene (CAS-No 26898-17-9) in the base paste was replaced by the same amount of bezene sulfonic acid N-butyl amide (CAS-No 3622-84-2), Entry 13.

Di-benzyl toluene (CAS-No 26898-17-9) in the base paste was replaced by the same amount of benzene sulfonic acid N-buty N-methyl amide (CAS-No 119059-69-7), Entry 15.

TABLE 6

| Entry | Sulphonamide | Amount of Sulfonamide in Elastomer | Amount of Sulfonamide in Base Paste | Shore-Hardness A after 6 min | 8 min | 10 min | 15 min | 30 min | 24 h |
|---|---|---|---|---|---|---|---|---|---|
| 13 | benzene sulfonic acid N-butyl amide | 3.75% | 6.00% | 30 | 37 | 42 | 46 | 50 | 50 |
| 15 | benzene sulfonic acid N-butyl N-methyl amide | 3.75% | 6.00% | 23 | 33 | 37 | 43 | 48 | 49 |

The invention claimed is:

1. A dental composition comprising:
   (a) an N-alkyl aziridine polyether,
   (b) a compound having an $SO_2$—NH group,
   wherein component (b) is selected from the group consisting of p-toluene sulfonic acid N-ethyl amide, o-toluene sulfonic acid N-ethyl amide, and a mixture of o-/p-toluene sulfonic acid N-ethyl amide; and
   (c) an initiator.

2. A dental composition comprising:
   (a) an N-alkyl aziridine polyether,
   (b) a compound having an $SO_2$—NH group,
   wherein component (b) comprises p-toluene sulfonic acid N-ethyl amide; and
   (c) an initiator.

3. The composition of claim 1, further comprising at least one additive selected from the group consisting of modifiers, fillers, dyes, pigments, thixotropic agents, flow improvers, polymeric thickeners, surfactants, odorous substances, diluting agents and flavouring agents.

4. The composition according to claim 1, wherein component (a) comprises a structural element represented by the following formula:

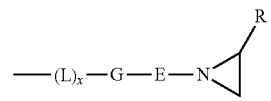

wherein

R is a moiety selected from the group consisting of H, $C_1$-$C_{12}$ alkyl, $C_2$-$C_{12}$ alkenyl, $C_2$-$C_{12}$ alkinyl, $C_7$-$C_{15}$ alkylaryl, $C_7$-$C_{15}$ arylalkyl, and $C_3$-$C_{12}$ cycloalkyl, wherein any of the hydrogen atoms of the moiety may be replaced by Cl or F and up to five carbon atoms of the moiety may be replaced by atoms or group of atoms selected from O, CO, N, and S, E is selected from the group consisting of $C_1$-$C_{18}$ branched or unbranched hydrocarbon chains wherein up to five carbon atoms of the chain may be replaced by an atom or group of atoms selected from O, CO, N, and S, G is a group selected from C(O)O, C(O)NR, C(O), C(O)C(O), C(O)(CH$_2$)$_m$C(O) where m is 1 to 10, C(S)NR, and CH$_2$, L is O, S, or NR and x is 0 or 1.

5. The composition of claim 1, wherein component (b) is o-toluene sulfonic acid N-ethyl amide.

6. The composition of claim 1, wherein initiator (c) is selected from the group consisting of protonating or alkylating agents or wherein the initiator (c) generates protons or reactive alkylating agents in a chemical reaction.

7. The composition of claim 1 having a working time at 23° C. of equal or less than 3:30 min according to DIN EN ISO 4823:2000 or an oral setting time of equal or less than 3:30 min.

8. The dental composition of claim 1, wherein the composition is a dental impression material.

9. The dental composition of claim 1, wherein the initiator comprises an alkyl sulfonium salt.

10. The dental composition of claim 1, wherein the Shore Hardness A measured after 6 minutes according to DIN EN ISO 53505 is greater than a value measured for the dental composition without component (b).

11. The dental composition of claim 10, wherein the Shore Hardness A measured after 6 minutes according to DIN EN ISO 53505 is more than 30% greater than the value measured for the dental composition without component (b).

12. A kit comprising a base part and a catalyst part, wherein the base part comprises an N-alkyl aziridine polyether, the catalyst part comprises an initiator, and wherein a compound selected from the group consisting of p-toluene sulfonic acid N-ethyl amide, o-toluene sulfonic acid N-ethyl amide, and a mixture of o-/p-toluene sulfonic acid N-ethyl amide is present either in the base part or the catalyst part or in the base part and the catalyst part
   in an amount of about 0.01% by weight to about 6.0% by weight.

13. A kit comprising a base part and a catalyst part, wherein the base part comprises an N-alkyl aziridine polyether, the catalyst part comprises an initiator, and wherein a compound selected from the group consisting of p-toluene sulfonic acid N-ethyl amide, o-toluene sulfonic acid N-ethyl amide, and a mixture of o-/p-toluene sulfonic acid N-ethyl amide is present in a further part in an amount of about 0.01% by weight to about 6.0% by weight and is not present in the catalyst part or in the base part.

14. A method of producing a dental composition comprising the step of mixing
   (a) an N-alkyl aziridine polyether,
   (b) a compound selected from the group consisting of p-toluene sulfonic acid N-ethyl amide, o-toluene sulfonic acid N-ethyl amide, and a mixture of o-/p-toluene sulfonic acid N-ethyl amide,
   present in an amount of about 0.01% by weight to about 6.0% by weight; and
   (c) an initiator.

15. A method for enhancing the setting speed of a dental composition, comprising an N-alkyl aziridine polyether, the method comprising the step of incorporating into the composition a compound selected from the group consisting of p-toluene sulfonic acid N-ethyl amide, o-toluene sulfonic acid N-ethyl amide, and a mixture of o-/p-toluene sulfonic acid N-ethyl amide,
   present in an amount of about 0.01% by weight to about 6.0% by weight.

16. The kit of claim 12, wherein the initiator comprises an alkyl sulfonium salt.

17. The kit of claim 13, wherein the initiator comprises an alkyl sulfonium salt.

18. The method of claim 14, wherein the initiator comprises an alkyl sulfonium salt.

19. The method of claim 15, wherein the initiator comprises an alkyl sulfonium salt.

* * * * *

UNITED STATES PATENT AND TRADEMARK OFFICE
CERTIFICATE OF CORRECTION

| | | |
|---|---|---|
| PATENT NO. | : 7,838,572 B2 | Page 1 of 1 |
| APPLICATION NO. | : 10/564102 | |
| DATED | : November 23, 2010 | |
| INVENTOR(S) | : Thomas Klettke | |

It is certified that error appears in the above-identified patent and that said Letters Patent is hereby corrected as shown below:

Title Page

After "Item [73] Assignee:", insert -- 3M ESPE AG, Seefeld, Germany --

Signed and Sealed this

Fourth Day of January, 2011

David J. Kappos
*Director of the United States Patent and Trademark Office*